United States Patent [19]

Enders et al.

[11] 4,112,065

[45] Sep. 5, 1978

[54] COMPOSITIONS OF BIS(ORTHO-SUBSTITUTED PHENYL)CARBODIIMIDES AND QUATERNARY AMMONIUM SALTS AND THEIR USE THEREOF IN COMBATTING ECTOPARASITIC TICK INFESTATIONS OF ANIMALS

[75] Inventors: Edgar Enders, Cologne; Wilhelm Stendel, Wuppertal; Herbert Voege, Leverkusen, all of Fed. Rep. of Germany

[73] Assignee: Bayer Aktiengesellschaft

[21] Appl. No.: 741,214

[22] Filed: Nov. 12, 1976

[30] Foreign Application Priority Data

Nov. 27, 1975 [DE] Fed. Rep. of Germany ....... 2553259

[51] Int. Cl.$^2$ .......................... A01N 9/06; A01N 9/20; A01N 9/24; A61K 9/04
[52] U.S. Cl. ...................................... 424/45; 424/304; 424/329; 424/330
[58] Field of Search .................. 424/45, 304, 329, 330

[56] References Cited

U.S. PATENT DOCUMENTS

| | | | |
|---|---|---|---|
| 3,157,662 | 11/1964 | Smeltz | 260/288 |
| 3,175,896 | 3/1965 | Arndt et al. | 424/330 |
| 3,280,137 | 10/1966 | Wakeman et al. | 424/329 |
| 3,366,672 | 1/1968 | Wakeman et al. | 424/329 |
| 3,487,156 | 12/1969 | Duerr et al. | 424/330 |
| 3,560,390 | 2/1971 | Gaines | 424/329 |
| 3,827,873 | 8/1974 | Shema et al. | 424/329 |
| 3,852,437 | 12/1974 | Helfenberger | 424/304 |
| 3,995,053 | 11/1976 | Kitaoka et al. | 424/304 |
| 3,996,378 | 12/1976 | Payton | 424/329 |
| 4,006,218 | 2/1977 | Sipos | 424/329 |

OTHER PUBLICATIONS

McCutcheon's "Detergents & Emulsifiers", 1971 annual – Allured Publ. Co., New Jersey – pp. 200 and 201.

*Primary Examiner*—Albert T. Meyers
*Assistant Examiner*—D. W. Robinson
*Attorney, Agent, or Firm*—Jacobs & Jacobs

[57] ABSTRACT

Mixtures of (a) bis-(2-X-phenyl)carbodiimides in which X is an alkyl or cycloalkyl group, which carbodiimide may be further substituted on each phenyl group by one or more halo, alkyl or cycloalkyl groups, and (b) quaternary ammonium compounds demonstrate superior ectoparasiticidal properties. Ectoparasiticidal compositions comprising these carbodiimides and quaternaries are described.

20 Claims, No Drawings

COMPOSITIONS OF BIS(ORTHO-SUBSTITUTED PHENYL) CARBODIIMIDES AND QUATERNARY AMMONIUM SALTS AND THEIR USE THEREOF IN COMBATTING ECTOPARASITIC TICK INFESTATIONS OF ANIMALS

DETAILED DESCRIPTION

The present invention pertains to mixtures of certain ortho, ortho-disubstituted diphenylcarbodiimides and quaternary ammonium compounds as ectoparasiticidal agents and to compositions comprising such mixtures for use in combatting ectoparasitic infestations.

Diphenylcarbodiimides are a well known class of compounds which have been previously described as stabilizers for polyurethane plastics; see e.g. Angew. Chem. 74, 801 (1962). Ammonium salts are also well known as surface-active agents, emulsifiers, foam preventatives, invert soaps, disinfectants, and especially as phase transfer catalysts; see e.g. E. V. Dehmlow, Angew. Chem. 86, 187 to 196 (1974); D. Landini et al., Synthesis 1975, 430 to 431; A. W. Herriott, Synthesis 1975, 447 to 448.

The present invention is based upon the discovery that mixtures of these diphenylcarbodiimides and quaternary compounds exhibit superior ectoparasiticidal properties, especially against ticks, and moreover on the discovery that these mixtures can be placed in stable combination with certain carriers in order to take advantage of this surprising property.

In a first embodiment, the invention pertains to compositions for combatting ectoparasites comprising an ectoparasiticidal amount of a mixture of (a) a bis-(2-X-phenyl)carbodiimide in which X is alkyl of 1 to 6 carbon atoms or cycloalkyl of 3 to 6 carbon atoms which carbodiimide is further unsubstituted or further substituted on each phenyl group with from one to three like or different substituents selected from the group consisting of halo, alkyl of 1 to 6 carbon atoms or cycloalkyl of 3 to 6 carbon atoms and (b) a quaternary ammonium compound having a total of from 10 to 50 carbon atoms in its cation, said salt being of the formula:

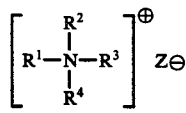

wherein (i) each of $R^1$, $R^2$, $R^3$ and $R^4$ when taken independently are like or different unsubstituted or substituted hydrocarbon units selected from the group consisting of alkyl, cycloalkyl, aralkyl or aryl, or (ii) $R^1$, $R^2$ and $R^3$ together with the nitrogen atom to which they are bound are a quaternary heterocyclic and $R^4$ is alkyl, cycloalkyl, aralkyl or aryl; and $Z\ominus$ is a monovalent anionic radical.

Preferably such a mixture is in stable combination with at least one cutaneously acceptable carrier selected from the group consisting of (i) a natural or synthetic solid mineral carrier, (ii) a liquified gaseous carrier; (iii) a normally liquid organic medium and (iv) an emulsified aqueous medium.

Within the foregoing class of carbodiimides, a preferred group are those of the formula:

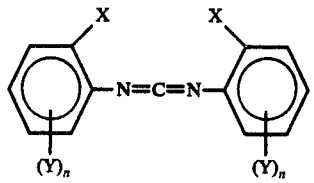

wherein
X is alkyl of 1 to 6 carbon atoms or cycloalkyl of 3 to 6 carbon atoms;
each of Y is independently chloro, bromo, alkyl of 1 to 6 carbon atoms or cycloalkyl of 3 to 6 carbon atoms; and
n has a value of 0, 1, 2 or 3

Preferably among the compounds of Formula II, X is methyl, ethyl, propyl, isopropyl, butyl, sec.butyl, tert.butyl, cyclopentyl or cyclohexyl.

In addition, it is preferred that the bis-(2-X-phenyl)-carbodiimide is further substituted on each phenyl with one to three like or different substituents selected from the group consisting of methyl, ethyl, propyl, isopropyl, butyl, sec.butyl, tert.butyl, cyclopentyl, cyclohexyl, bromo or chloro.

Within the foregoing class of quaternary ammonium compounds, a preferred group are those wherein each of $R^1$, $R^2$, $R^3$ and $R^4$, when taken independently, is phenyl or alkyl of 1 to 20 carbon atoms, unsubstituted or substituted by phenyl, phenoxy, chlorophenyl, alkylphenyl, alkylphenoxy or oxo, or $R^1$, $R^2$ and $R^3$, when taken together are pyridinyl, imidazolyl, thiazolyl, quinolyl, or isoquinolyl and $Z\ominus$ is hydroxy, chloro, bromo, iodo, methylsulfonato, ethylsulfonato, tolylsulfonato, methylsulfato or ethylsulfato.

In a further embodiment the invention pertains to a method of combatting ectoparasitic infestation in animals which comprises applying to the skin of an animal an ectoparasiticidal amount of a mixture of (a) a bis-(2-X-phenyl)carbodiimide in which X is alkyl of 1 to 6 carbon atoms or cycloalkyl of 3 to 6 carbon atoms which carbodiimide is further unsubstituted or further substituted on each phenyl group with from one to three like or different substituents selected from the group consisting of halo, alkyl of 1 to 6 carbon atoms or cycloalkyl of 3 to 6 carbon atoms.

Preferably in this method, the mixture is applied in the form of a composition according to the invention; i.e. the mixture is applied in stable combination with at least one cutaneously acceptable carrier selected from the group consisting of (i) a natural or synthetic solid mineral carrier, (ii) a liquified gaseous carrier, (iii) a normally liquid organic medium and (iv) an emulsified aqueous medium.

Heretofore ectoparasiticidal agents for use particularly against ticks have included such classes as N-aryl-N'-alkylformamidines, N-alkyl-2-aryliminopyrrolidines, thiourea derivatives and other sulfur containing compounds, particularly against strains of ticks which have proved resistant to phosphoric acid esters. It is thus surprising that the bis-(ortho-substituted phenyl)carbodiimides, which possess no structural similarity to known ectoparasiticidal agents, demonstrate this type of property. It is also surprising that these compounds can be formulated into stable compositions without decomposing through hydrolysis since the conversion of diarylcarbodiimides to diarylureas through the acid or base catalyzed addition of water is well known; see e.g. Chem. Rev., 67, 117 (1967). Finally, it is surprising that this combination provides a synergistic effect since the quaternary ammonium compounds demonstrate little if any ectoparasiticidal activity.

The bis-(ortho-substituted phenyl)carbodiimides are known or can be readily prepared in accordance with known processes, see e.g. W. Newmann and P. Fischer, Angew, Chem., 74, 801-806 (1962); H. G. Khorana, Chem. Rev., 53, 145-166 (1953); F. Kurzer and K. Douraghi-Zadeh, Chem. Rev., 67, 107-152 (1967).

In the Formula II, X and Y represent straight-chain or branched alkyl with, preferably, 1 to 6, especially 1 to 4, carbon atoms. Examples which may be mentioned are methyl, ethyl, n-propyl, isopropyl, n-butyl, isobutyl, sec.butyl and tert.butyl. These groups can also be cycloalkyl of 3 to 6 carbon atoms such as cyclopropyl, cyclobutyl, cyclopentyl and cyclohexyl.

When Y is halogen, it is, in general, fluoro, chloro, bromo or iodo, preferably chloro or bromo.

When n is greater than 1, the plurality of substituents represented by Y can be like or different. Moreover, while from the standpoint of synthetic ease the compounds will generally be symmetrically substituted, the two phenyl groups can have different patterns of substitution.

Examples of the diphenylcarbodiimides which can be used according to the invention include 2,6,2',6'-tetramethyldiphenylcarbodiimide, m. 49°-50° C; 2,4,2',4'-tetramethyldiphenylcarbodiimide, b. 188'-192° C/0.4 mm Hg; 2,4,2',4'-tetramethyl-6,6'-diisopropyldiphenylcarbodiimide; 2,4,2',4'-tetramethyl-6,6'-dichlorodiphenylcarbodiimide; 2,2'-dimethyl-6,6'-diethyldiphenylcarbodiimide; 2,2',6,6'-tetraethyldiphenylcarbodiimide, b. 135°-138° C/0.02 mm Hg; 2,4,2',4'-tetraethyldiphenylcarbodiimide; 2,2',6,6'-tetraethyl-3,3'-dimethyldiphenylcarbodiimide, b. 197°-200° C/1.5 mm Hg; 2,2',6,6'-tetraethyl-3,3'-dichlorodiphenylcarbodiimide, b. 166°-172° C/0.05 mm Hg; 2,2',6,6'-tetraethyl-4,4'-dimethyldiphenylcarbodiimide, b. 176°-178° C/0.035 mm Hg; 2,2'-diisopropyldiphenylcarbodiimide; 2,2'-di-sec.butyldiphenylcarbodiimide; 2,2'-di-tert.-butyldiphenylcarbodiimide; 2,2'-di-cyclopentyldiphenylcarbodiimide; 2,2'-dimethyl-6,6'-di-isopropyldiphenylcarbodiimide, b. 186°-190° C/2.0 mm Hg; 2,2',6,6'-tetraisopropyldiphenylcarbodiimide; 2,6,2',6'-tetraethyl-3,5,3',5'-tetramethyldiphenylcarbodiimide; 2,6,2',6'-tetra-sec.butylcarbodiimide, b. 170°-180° C/0.04 mm Hg; 2,6,2',6'-tetraisopropyl-4,4'-dibromodiphenylcarbodiimide, m. 115°-116° C; 2,6,2',6'-tetraisopropyl-4,4'-dichlorodiphenylcarbodiimide, m. 100°-105° C; 2,2'-di-tert.butyl-4,4'-dimethyldiphenylcarbodiimide; 2,2'-di-tert.butyl-4,4'-dimethyl-6,6'-dichlorodiphenylcarbodiimide; 2,2'-dimethyl-4,4'-dicyclohexyldiphenylcarbodiimide; 2,2',6,6'-tetracyclopentyldiphenylcarbodiimide, m. 92°-95° C; 2,6-diisopropyl-2',6'-diethyldiphenylcarbodiimide; 2,6-diisopropyl-2',4'-dimethyldiphenylcarbodiimide; 2,6-diisopropyl-2',6'-di-sec.butyldiphenylcarbodiimide; 2,6-diisopropyl-2'-methyl-6'-chlorodiphenylcarbodiimide; 2,6-diisopropyl-2',4',5'-trimethyldiphenylcarbodiimide; 2,6-diisopropyl-2',4',5'-trimethyldiphenylcarbodiimide and 2,2'-dimethyl-4,4'-dichlorodiphenylcarbodiimide, m. 50°-51° C.

Diphenylcarbodiimides, both known and new, can be prepared by reacting corresponding isocyanates with phosphine oxides. The reaction can be illustrated by the following equation:

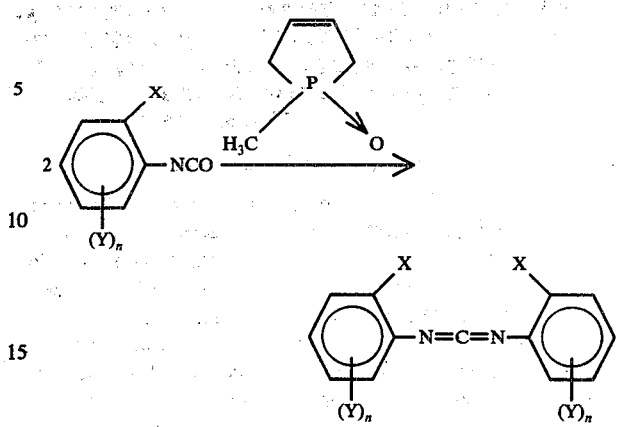

The quaternary ammonium compounds are also known or can be readily prepared in accordance with known processes, as for example in J. Gorderler in Houben-Weyl "Methoden der organischen Chemie", Vol. 11/2, pp 589-640.

The optionally substituted alkyl groups $R^1$, $R^2$, $R^3$ and $R^4$ can be any desired straight-chain and/or branched, optionally substituted, alkyl group with 1 to 20 carbon atoms, the number of carbon atoms in $R^1$ to $R^4$ in total being 10 or 50, preferably 16 to 40.

Preferred aralkyl groups for $R^1$, $R^2$, $R^3$ and $R^4$ are aralkyl groups with 6 to 10, especially 6, carbon atoms in the aryl part and preferably 1 to 4, especially 1 or 2, carbon atoms in the alkyl part, it being possible for the alkyl part to be straight-chain or branched. Benzyl and phenethyl may be mentioned as examples.

Preferred aryl groups for $R^1$, $R^2$, $R^3$ and $R^4$ are those with 6 or 10 carbon atoms, particularly phenyl or naphthyl.

Typical substituents for alkyl groups embraced by $R^1$, $R^2$, $R^3$ and $R^4$ are those generally customary in nitrogen-containing cation-active compounds, particularly phenoxy, dodecylaminocarbonyl and 2-(p-isooctylphenoxy)-ethoxy.

$R^1$, $R^2$ and $R^3$ can, together with the nitrogen atom to which they are bound, form a quaternary monocyclic or bicyclic heterocyclic ring system, preferably with 5 or 6 ring members in the heterocyclic part, as for example, pyridine, imidazole, thiazole, quinoline and isoquinoline.

The monovalent anionic radical $Z\ominus$ is preferably one equivalent of an anion of an inorganic or organic acid or a hydroxyl ion; in particular, $Z\ominus$ represents chloride, bromide and iodide, the alkylsulphonato radical such as $CH_3-SO_3\ominus$ or $C_2H_5-SO_3\ominus$, or the

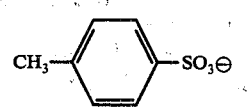

radical, the alkylsulfato radical such as $CH_3-O-SO_3\ominus$ or $C_2H_5O-SO_3\ominus$, and the hydroxyl ion.

Typical quaternary ammonium compounds include (benzyl)-tri-(methyl)-ammonium chloride, (benzyl)-tri-(methyl)-ammonium hydroxide, (benzyl)-tri-(methyl)-ammonium bromide, (4-chlorobenzyl)-tri-(ethyl)-ammonium chloride, (β-phenethyl)-tri-(ethyl)- ammonium chloride, (benzyl)-tri-(butyl)-ammonium chloride, di(benzyl)-di(methyl)-ammonium chloride, (β-phenoxyethyl)-tri-(ethyl)-ammonium chloride, (benzyl)-(dodecyl)di(methyl)-ammonium chloride; (benzyl)-(hexadecyl)-di(methyl)ammonium chloride, (benzyl)-(phenyl)-di(methyl)-ammonium chloride, (benzyl)-(4-methylphenyl)-di(ethyl)-ammonium chloride, (benzyl)-(dodecylaminocarbonylmethyl)-di(methyl)-ammonium chloride, (benzyl)[5-(4-isooctylphenoxy)-3-oxapentyl]-di(methyl)-ammonium chloride, tri(butyl)-methylammonium methosulfate, tetra(butyl)-ammonium bisulfate, tri(hexyl)-methylammonium bromide, di-(cyclohexyl)-di-(methyl)-ammonium toluenesulphonate, tri(octyl)-methylammonium iodide, (hexadecyl)-tri-(methyl)-ammonium bromide, (pentadecyl)tri-(methyl)-ammonium chloride, di-(octadecyl)-di(methyl)ammonium chloride, hexadecyl-pyridinium chloride, dodecylpyridinium bromide, dodecyl-quinolinium bromide, 1-hexadecyl-3-methylimidazolium chloride and 1-dodecyl-3-benzylimidazolium chloride.

The weight ratios of the components in the combination can vary within relatively large ranges. In general, 0.05 to 3 parts by weight of quaternary ammonium compound, and preferably 0.2 to 2 parts by weight, are utilized per part by weight of diphenylcarbodiimide.

The compositions according to the invention, which contain the diphenylcarbodiimides and the quaternaries, exhibit powerful ectoparasiticidal properties, especially, against ticks, which as animal ectoparasites infest domesticated animals, such as cattle and sheep. At the same time, the active compounds according to the invention have low toxicity for warm-blooded animals. They are therefore very suitable for combatting animal ectoparasites, especially ticks.

Examples of economically important ectoparasites of this type, which play a large role particularly in tropical and sub-tropical countries, include the Australian and South American one-host cattle tick *Boophilus microplus*, the South African cattle tick *Boophilus decoloratus*, (both from the family of the Ixodidae), African polyvalent cattle ticks and sheep ticks, such as *Rhipicephalus appendiculatus, Rhipicephalus evertsi, Amblyomma hebraeum* and *Hyalomma aruncatum*, and South American polyvalent cattle ticks, such as *Amblyomma cajennense* and *Amblyomma americanum*.

In the course of time, ticks in numerous areas have become resistant to the phosphoric acid esters and carbamates hitherto used so that the success in combatting infestation is becoming increasingly questionable. Economical animal raising in the infested areas urgently needs agents by means of which all stages of development (larvae, metalarvae, nymphs, metanymphs and adults) can be combatted reliably. This is particularly true for resistant strains such as those of the genus Boophilus. In Australia, for example, the Mackay strain, the Mt.-Alfort strain and the Biarra strain of *Boophilus microplus* are highly resistant to the phosphoric acid ester agents used hitherto.

The compounds utilized in the present invention are equally effective both against the normally sensitive and against the resistant strains. When applied to the skin of the host animal, they have a direct destructive effect on all forms which are parasitic on the animal, the cycle of development of the ticks thereby being interrupted in the parasitic phase on the animal. The laying of fertile eggs, and hence the development and slipping of larvae, in particular, is inhibited.

The agents can be used, for example, in a dip or bath. In this case the compounds must remain stable in the aqueous dip liquid, which can be contaminated and exposed to microbial attack, for six months or more. The compounds used in the present invention are completely stable and a decrease in action is not ascertainable even after six months.

The compounds can be formulated to give ectoparasiticidal compositions suitable for external or cutaneous application, for example by mixing the active compounds with certain additives. These include liquid, solid or liquefied gaseous diluents or carriers with, in the case of aqueous media, surface-active materials, as for example, an emulsifier or dispersing agent. Organic solvents can also be used as auxiliaries in such aqueous media.

Liquid organic media, in addition to water, include aromatic hydrocarbons, such as xylenes, toluene, benzene or alkylnaphthalenes; chlorinated aromatic or aliphatic hydrocarbons, such as chlorobenzenes, chloroethylenes or methylene chloride; aliphatic hydrocarbons, such as cyclohexane or paraffins, for example, mineral oil fractions with boiling ranges between 120° and 400° C, preferably 180° to 300° C; alcohols, such as butanol or ethylene glycol, as well as their ethers and esters; ketones, such as acetone, methyl ethyl ketone, methyl isobutyl ketone or cyclohexanone; and strongly polar solvents, such as dimethylformamide, dimethylsulfoxide, pyrrolidone, N-methylpyrrolidone or acetonitrile.

Liquefied gaseous diluents or carriers are liquids which would be gaseous at room temperature under normal pressure, for example aerosol carriers, such as, for example, halogenated hydrocabons. Freon may be mentioned as an example.

Solid diluents or carriers used preferentially are natural mineral substances, such as kaolins, chalks, talc, quartz, attapulgite, montmorillonite or diatomaceous earth, or synthetic mineral substances, such as, for example, highly disperse silica, aluminium oxide or silicates.

Preferred emulsifiers which can be used are non-ionic and anionic emulsifiers, such as, for example, polyoxyethylene-fatty acid esters, polyoxyethylene-fatty alcohol ethers, for example alkylaryl polyglycol ethers, alkylsulphonates, alkylsulphonates and arylsulphonates.

Examples of preferred dispersing agents are lignin, sulphite waste liquor and methylcellulose.

The ectoparasiticidal compositions of the present invention contain 0.1 to 95% by weight, preferably 0.5 to 90% by weight, of the mixture.

For the purpose of application, they can be diluted, for example with water. Depending on the form in which they are used, the concentrations can be varied over a wide range, in general from about 10 to about 50,000 ppm and preferably 50 to 10,000 ppm.

Other additives such as, for example, disinfectants or insecticides, can be added to the ready-to-use formulation.

The following examples will serve to typify the nature of the invention without being a limitation on the scope thereof.

EXAMPLE 1

2,6,2',6'-Tetraisopropyl-4,4'-dichlorodiphenylcarbodiimide 2,6'Diisopropyl-4-chlorophenyl isocyanate 0.5 g of anhydrous iron-III chloride is added to 376 g of 2,6-diisopropyl-phenyl isocyanate and 143 g of chlorine are passed in at 20°–40° C. The mixture is then slowly warmed to 120° C until the evolution of HCl has ceased. 3 g of anhydrous sodium sulfate are then added and the batch is fractionated in vacuo. Boiling point: 117°–120° C/2.5 mm Hg. Yield 250 g.

b. 2,6,2',6'-Tetraisopropyl-4,4'-dichloro-diphenylcarbodiimide

3 Drops of P-methyl-phospholine oxide are added to 40 g of 2,6-diisopropyl-4-chlorophenyl isocyanate and the mixture is warmed to 100°–120° C for about 8 hours, until the elimination of $CO_2$ has ceased. Yield 35 g. The product can be purified by recrystallization from petroleum ether. Melting point: 100°–105° C.

The elementary analysis and NMR spectrum agree with the assumed structure.

EXAMPLE 2

2,6,2',6'-Tetraisopropyl-4,4'-dibromo-diphenylcarbodiimide a. 2,6-Diisopropyl-4-bromophenyl isocyanate 0.5 g of anhydrous iron-III chloride is added to 203 g of 2,6-diisopropyl-phenyl isocyanate and 162 g of bromine are added dropwise at 20° C. The mixture is then slowly warmed to 120° C until the evolution of gas has ceased. 3.0 g of anhydrous sodium sulfate are then added and the mixture is fractionated in vacuo.

Boiling point 128°–135° C/3.0 mm Hg; yield 164 g.

The elementary analysis and NMR spectrum agree with the assumed structure.

b. 2,6,2',6'-Tetraisopropyl-4,4'-dibromo-diphenylcarbodiimide

3 Drops of P-methyl-phospholine oxide are added to 40.0 g of 2,6-diisopropyl-4-bromophenyl isocyanate and the mixture is warmed to 100°–120° C for about 4 hours, until the evolution of $CO_2$ has ended. The product solidifies on cooling. Yield 35 g; melting point 115°–116° C after recrystallization from petroleum ether.

The elementary analyses and NMR spectrum agree with the assumed structure.

EXAMPLE 3

In vitro tick test on Boophilus microplus

3 Parts of active compound are mixed with 7 parts of a mixture of equal parts by weight of ethylene glycol monomethyl ether and nonylphenol polyglycol ether. The emulsion concentrate thus obtained is diluted with water to the use concentration illustrated in the following table.

Adult fully bloated female ticks of the species *Boophilus microplus* (Biarra strain) are dipped for one minute into this preparation of active compound. After dipping groups of 25 female specimens, the individual ticks are transferred into plastic dishes, the bottom of which is lined with a disc of filter paper.

After 35 days, the effectiveness of the active compound preparation is determined by assessing the inhibition of laying of fertile eggs compared to the laying of eggs by untreated control ticks. The action is indicated in percent, with 100% denoting the fertile eggs were no longer laid and 0% denoting that ticks laid eggs in the normal manner, like the untreated control ticks.

Table 1

| Compound | Concentration (ppm) | % Inhibition |
|---|---|---|
| A | 4,096 | 100 |
| A | 2,048 | 80 |
| A | 1,024 | 40 |
| A | 512 | 25 |
| A | 256 | 0 |
| B | 4,096 | 50 |
| B | 2,048 | 0 |
| B | 1,024 | 0 |
| B | 512 | 0 |
| B | 256 | 0 |
| C | 4,096 + 4,096 | 100 |
| C | 2,048 + 2,048 | 100 |
| C | 1,024 + 1,024 | 95 |
| C | 512 + 512 | 60 |
| C | 256 + 256 | 30 |

A = 2,6,2',6'-Tetraisopropyldiphenylcarbodiimide.
B = Benzyldodecyldimethylammonium chloride.
C = Mixture of equal parts of 2,6,2',6'-tetraisopropyldiphenylcarbodiimide and benzyldodecyldimethylammonium chloride.

EXAMPLE 4

In vivo tick test on Boophilus microplus

3 Parts of active compound are mixed with 7 parts of a mixture of equal parts by weight of ethylene glycol monomethyl ether and nonylphenyl polyglycol ether. The emulsion concentrate thus obtained is diluted with water to the use concentration illustrated in the following table.

Cattle which have been repeatedly infected (12 x infections at intervals of 2 days) with resistant tick larvae of the species *Boophilus microplus*, Biarra strain, are sprayed with the active compound preparation thus obtained.

The action of the active compound preparation is determined by assessing the number of adult female ticks which develop on the treated cattle. This number is compared with the number of adult female ticks which develop on untreated cattle. A compound is the more active, the fewer female ticks develop after the treatment.

Table 2

| | | | Boophilus microplus (Biarra strain): All stages of development in vivo (cattle) | | | | | | | |
|---|---|---|---|---|---|---|---|---|---|---|
| | | | Number of ticks which lay fertile eggs | | | | | | | |
| | Concentration | Days before treatment | Days after treatment | | | | | | | |
| Compound | (ppm) | −2 – ±0 | +1–3 | +4–6 | +7–9 | +10–12 | +13–15 | +16–18 | +19–21 | 1–21 |
| | 5,000 | 768 | 23 | 1 | 11 | 20 | 13 | 5 | 0 | 73 |
| A | 3,000 | 415 | 50 | 11 | 47 | 43 | 3 | 0 | 0 | 154 |

Table 2-continued

| | | Boophilus microplus (Biarra strain): All stages of development in vivo (cattle) | | | | | | | | |
|---|---|---|---|---|---|---|---|---|---|---|
| | | | Number of ticks which lay fertile eggs | | | | | | | |
| | Concentration | Days before treatment | | | | Days after treatment | | | | |
| Compound | (ppm) | −2 − ±0 | +1-3 | +4-6 | +7-9 | +10-12 | +13-15 | +16-18 | +19-21 | 1-21 |
| B | 1,000 | 425 | 301 | 55 | 111 | 55 | 19 | 0 | 0 | 541 |
| | 1,000 + 1,000 | 1,066 | 7 | 0 | 0 | 0 | 0 | 0 | 0 | 7 |
| Untreated control | | 1,286 | 1,464 | 792 | 659 | 224 | 2,048 | 784 | 724 | 6,745 |

A = 2,6,2',6'-Tetraisopropyldiphenylcarbodiimide.
B = Mixture of 2,6,2',6'-tetraisopropyldiphenylcarbodiimide and benzyldodecyldimethylammonium chloride.

What is claimed is:

1. A composition for combatting ectoparasitic ticks of domesticated animals comprising a tickicidally effective amount of a mixture of (a) a bis-(2-X-phenyl)carbodiimide in which X is alkyl of 1 to 6 carbon atoms or cycloalkyl of 3 to 6 carbon atoms which carbodiimide is further unsubstituted or further substituted on each phenyl group with from one to three like or different substituents selected from the group consisting of halo, alkyl of 1 to 6 carbon atoms and cycloalkyl of 3 to 6 carbon atoms and (b) from 0.05 to 3 parts by weight of said carbodiimide of a quaternary ammonium salt having a total of from 10 to 50 carbon atoms in its cation, said salt being of the formula:

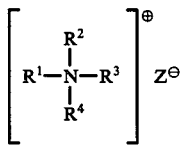

wherein each of $R^1$, $R^2$, $R^3$ and $R^4$ are like or different unsubstituted or substituted hydrocarbon units selected from the group consisting of alkyl, cycloalkyl, aralkyl and aryl and $Z^\ominus$ is a monovalent anionic radical.

2. A composition according to claim 1 wherein said mixture is in stable combination with at least one cutaneously acceptable carrier selected from the group consisting of (i) a natural or synthetic solid mineral carrier, (ii) a liquified gaseous carrier; (iii) a normally liquid organic medium and (iv) an emulsified aqueous medium.

3. A composition according to claim 1 wherein said bis-(2-X-phenyl)carbodiimide is of the formula:

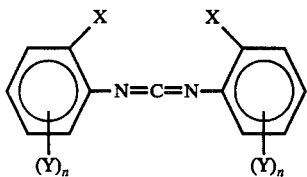

wherein
X is alkyl of 1 to 6 carbon atoms or cycloalkyl of 3 to 6 carbon atoms;
each Y is independently chloro, bromo, alkyl of 1 to 6 carbon atoms or cycloalkyl of 3 to 6 carbon atoms; and
n has a value of 0, 1, 2 or 3

4. A composition according to claim 3 wherein in said bis-(2-X-phenyl)carbodiimide, X is methyl, ethyl, propyl, isopropyl, butyl, sec.butyl, tert.butyl, cyclopentyl or cyclohexyl.

5. A composition according to claim 4 wherein said bis-(2-X-phenyl)carbodiimide is further substituted on each phenyl with one to three like or different substituents selected from the group consisting of methyl, ethyl, propyl, isopropyl, butyl, sec.butyl, tert.butyl, cyclopentyl, cyclohexyl, bromo and chloro.

6. A composition according to claim 1 wherein each of $R^1$, $R^2$, $R^3$ and $R^4$ is phenyl or alkyl of 1 to 20 carbon atoms, unsubstituted or substituted by phenyl, phenoxy, chlorophenyl, alkylphenyl, alkylphenoxy or oxo, and $Z^\ominus$ is hydroxy, chloro, bromo, iodo, methylsulfonato, ethylsulfonato, tolylsulfonato, methylsulfato or ethylsulfato.

7. A composition according to claim 6 wherein said quaternary ammonium salt is selected from the group consisting of (benzyl)-tri-(methyl)-ammonium chloride, (benzyl)-tri-(methyl)-ammonium hydroxide, (benzyl)-tri-(methyl)-ammonium bromide, (4-chlorobenzyl)-tri-(ethyl)-ammonium chloride, (β-phenethyl)-tri-(ethyl)-ammonium chloride, (benzyl)-tri-(butyl)-ammonium chloride, di(benzyl)-di(methyl)-ammonium chloride, (β-phenoxyethyl)-tri-(ethyl)-ammonium chloride, (benzyl)-(dodecyl)-di(methyl)-ammonium chloride; (benzyl)-(hexadecyl)-di(methyl)-ammonium chloride, (benzyl)-(phenyl)-di(methyl)-ammonium chloride, (benzyl)-(4-methylphenyl)-di(ethyl)-ammonium chloride, (benzyl)-(dodecylaminocarbonylmethyl)-di(methyl)-ammonium chloride, (benzyl)-[5-(4-isooctylphenoxy)-3-oxapentyl]-di(methyl)-ammonium chloride, tri(butyl)-methylammonium methosulfate, tetra(butyl)-ammonium bisulfate, tri(hexyl)-methylammonium bromide, di(cyclohexyl)-di-(methyl)-ammonium toluenesulphonate, tri(octyl)-methylammonium iodide, (hexadecyl)-tri-(methyl)-ammonium bromide, (pentadecyl)-tri-(methyl)-ammonium chloride and di-(octadecyl)-di(-methyl)-ammonium chloride.

8. A composition according to claim 1 wherein the weight ratio of said bis-(2-X-phenyl)carbodiimide to said quaternary ammonium salt is from 1:0.2 to 1:2, respectively.

9. A composition according to claim 1 wherein said carrier is a natural or synthetic mineral carrier.

10. A composition according to claim 1 wherein said carrier is a liquified gaseous carrier.

11. A composition according to claim 1 wherein said carrier is a normally liquid organic medium.

12. A composition according to claim 1 wherein said carrier is an emulsified aqueous medium.

13. A composition according to claim 1 wherein said mixture consists of 2,6,2', 6'-tetraisopropyl-diphenylcarbodiimide and (benzyl)-(dodecyl)-di(methyl)-ammonium chloride.

14. The method of combatting ectoparasitic tick infestation of domesticated animals which comprises applying to the skin of an animal a tickicidally effective amount of a mixture of (a) a bis-(2-X-phenyl)-carbodiimide in which X is alkyl of 1 to 6 carbon atoms of cycloalkyl of 3 to 6 carbon atoms which carbodiimide is further unsubstituted or further substituted on each phenyl group with from one to three like or different substituents selected from the group consisting of halo, alkyl of 1 to 6 carbon atoms and cycloalkyl of 3 to 6 carbon atoms and (b) from 0.005 to 3 parts, by weight of said carbodiimide, of a quaternary ammonium salt having a total of from 10 to 50 carbon atoms in its cation, said salt being of the formula:

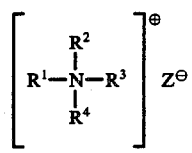

wherein each of $R^1$, $R^2$, $R^3$ and $R^4$ are like or different unsubstituted or substituted hydrocarbon units selected from the group consisting of alkyl, cycloalkyl, aralkyl and aryl, and $Z^\ominus$ is a monovalent anionic radical.

15. The method according to claim 14 wherein said mixture is applied in stable combination with at least one cutaneously acceptable carrier selected from the group consisting of (i) a natural or synthetic solid mineral carrier, (ii) a liquified gaseous carrier, (iii) a normally liquid organic medium and (iv) an emulsified aqueous medium.

16. The method according to claim 15 wherein said carrier is a natural or synthetic mineral.

17. The method according to claim 15 wherein said carrier is a liquified gaseous carrier.

18. The method according to claim 15 wherein said carrier is a normally liquid organic medium.

19. The method according to claim 15 wherein said carrier is an emulsified aqueous medium.

20. The method according to claim 14 wherein said mixture consists of 2,6,2',6'-tetraisopropyl-diphenylcarbodiimide and (benzyl)-(dodecyl)-di(methyl)-ammonium chloride.

* * * * *